United States Patent
Frembgen

(10) Patent No.: US 9,463,292 B2
(45) Date of Patent: Oct. 11, 2016

(54) METABOLIC SIMULATOR

(75) Inventor: Stefan Frembgen, Pittsburgh, PA (US)

(73) Assignee: IngMar Medical, Ltd., Pittsburgh, PA (US)

( * ) Notice: Subject to any disclaimer, the term of this patent is extended or adjusted under 35 U.S.C. 154(b) by 1044 days.

(21) Appl. No.: 13/232,662

(22) Filed: Sep. 14, 2011

(65) Prior Publication Data

US 2012/0060933 A1   Mar. 15, 2012

Related U.S. Application Data

(60) Provisional application No. 61/382,616, filed on Sep. 14, 2010.

(51) Int. Cl.
| | | |
|---|---|---|
| *A61M 16/00* | (2006.01) | |
| *A61M 16/10* | (2006.01) | |
| *H01M 8/10* | (2016.01) | |

(52) U.S. Cl.
CPC ............. *A61M 16/00* (2013.01); *A61M 16/10* (2013.01); *A61M 2016/103* (2013.01); *H01M 8/1011* (2013.01); *Y02E 60/523* (2013.01); *Y10T 137/0329* (2015.04)

(58) Field of Classification Search
CPC ........... A61M 16/00; A61M 16/0051; A61M 16/12; A61M 16/10; A61M 2016/103; A61M 2016/102; G09B 23/00; G09B 23/28; G09B 23/288
USPC ............ 128/204.22, 200.24, 202.13, 202.16, 128/202.26; 73/23.2; 95/51, 52, 54, 117, 95/138, 139
See application file for complete search history.

(56) References Cited

U.S. PATENT DOCUMENTS

| | | | |
|---|---|---|---|
| 3,049,812 A | 1/1961 | Bovard | |
| 5,584,701 A | 12/1996 | Lampotang et al. | |
| 5,975,748 A | 11/1999 | East, IV et al. | |
| 6,957,651 B2 | 10/2005 | Nuckols et al. | |
| 7,959,443 B1 | 6/2011 | Frembgen et al. | |
| 2007/0077466 A1* | 4/2007 | Akiyama et al. | ............... 429/22 |
| 2008/0283062 A1* | 11/2008 | Esposito, Jr. | ............ 128/204.23 |
| 2008/0292918 A1* | 11/2008 | Finnerty et al. | ................ 429/13 |
| 2008/0314386 A1* | 12/2008 | Myklebust et al. | ..... 128/205.15 |
| 2009/0107501 A1* | 4/2009 | Krieger | .................... 128/204.23 |

OTHER PUBLICATIONS

Duffield, et al., "Redesign of the Human Metabolic Simulator", SAE Publication No. 2004-01-2497, 34th International Conference on Environmental Systems (ICES), Jul. 19-22, 2004.
Gemma Crawley, "Direct Methanol Fuel Cells (DMFC)", Fuel Cell Today, Aug. 2007, pp. 1-13, www.fuelcelltoday.

* cited by examiner

*Primary Examiner* — Justine Yu
*Assistant Examiner* — Colin W Stuart
(74) *Attorney, Agent, or Firm* — The Webb Law Firm

(57) ABSTRACT

A respiratory metabolic simulator includes a cell that produces $CO_2$ and depletes $O_2$, e.g., a direct methanol fuel cell having an external electrical circuit. An electric load is applied to the external electrical circuit of the direct methanol fuel cell to vary the electrical load applied to the external electrical circuit of the direct methanol fuel cell to produce carbon dioxide. The carbon dioxide generated by the direct methanol fuel cell is supplied to respiration gases produced by the respiratory metabolic simulator. The direct methanol fuel cell is also used to remove oxygen from the respiration gases prior to mixing the respiration gases and the carbon dioxide.

6 Claims, 5 Drawing Sheets

METABOLIC SIMULATOR

CROSS REFERENCE TO RELATED APPLICATIONS

This application claims the benefit of United States Provisional Patent Application No. 61/382,616, filed Sep. 14, 2010, and entitled "Metabolic Simulator". This application relates to U.S. Provisional Patent Application No. 61/534,696, filed Sep. 14, 2011, entitled "Metabolic Simulator Having a Catalytic Engine". The contents of both applications are incorporated herein by reference.

BACKGROUND OF THE INVENTION

1. Field of the Invention

The present invention is directed to a simulator and, more particularly, to a metabolic simulator (MS) or a respiratory metabolic simulator (RMS), wherein carbon dioxide ($CO_2$) is supplied and/or oxygen ($O_2$) is removed using a cell that produces $CO_2$ and depletes $O_2$, e.g., a direct methanol fuel cell (DMFC).

2. Description of Related Art

For the purpose of providing a realistic "load" for life-supporting devices and environments it is sometimes necessary to simulate a human's impact as far as exhaled breathing gases and caloric output are concerned. Simulators to that effect are called metabolic simulators (MS) or respiratory metabolic simulators (RMS). It is not always necessary to mimic all output gas concentrations with high fidelity or the dissipation of heat caused by the presence of a person, so that for some purposes the addition of $CO_2$ to the gas exhaled by a breathing simulator is sufficient.

The prior art relating to the addition of $CO_2$ and/or removal of $O_2$ in a full RMS discloses a means for controlled combustion of organic fuels (U.S. Pat. No. 3,049,812 to Bovard) and a system for full or partial gas substitution (U.S. Pat. No. 5,584,701 to Lampotang et al.; and Duffield et al., "Redesign of the Human Metabolic Simulator, SAE Publication No. 2004-01-2497, 34th International Conference on Environmental Systems (ICES), Jul. 19-24, 2004). In addition, using a hydrogen-fueled catalytic process as a means of $O_2$ reduction and $CO_2$ production has been disclosed (U.S. Pat. No. 6,957,651 to Nuckols et al.) but has not been implemented in the NASA Human Metabolic Simulator due to safety concerns and other technical considerations.

As can be appreciated by those skilled in the art, it would be advantageous to provide an MS and/or an RMS that has a process to reduce $O_2$ and to produce $CO_2$ that does not have the limitations of the hydrogen-fueled catalytic process of the prior art.

SUMMARY OF THE INVENTION

The present invention includes a respiratory metabolic simulator (RMS) in which $CO_2$ additions and $O_2$ reduction are achieved using a DMFC. More particularly, one non-limiting embodiment of the invention is directed to a respiratory metabolic simulator including, among other things, a direct methanol fuel cell having an external electrical circuit, facilities for applying an electrical load to the external electrical circuit of the direct methanol fuel cell, facilities for varying the electrical load applied to the external electrical circuit of the direct methanol fuel cell, and facilities for supplying carbon dioxide generated by the direct methanol fuel cell to respiration gases produced by the respiratory metabolic simulator, wherein, by varying the electrical load, an amount of carbon dioxide generated by the direct methanol fuel cell and provided to the respiration gases produced by the respiratory metabolic simulator is controlled.

Another embodiment of the present invention is directed to an improved system for delivering $CO_2$ in a respiration closed-loop control system to a respiratory simulator, the system includes, among other things, a piston/cylinder arrangement having a first inlet for receiving a volume of air during an inhalation phase; a second inlet for receiving $CO_2$; and an outlet for releasing the air and $CO_2$ therethrough during an exhalation phase; a stored supply of $CO_2$, the supply connected to the piston/cylinder arrangement via a fluid path; a valve situated along the fluid path between the $CO_2$ supply and the piston/cylinder arrangement; a diffusing surface situated within the piston/cylinder arrangement for distributing the $CO_2$ within the cylinder; and a controller configured to actuate the valve to allow a predefined amount of $CO_2$ to flow into the piston/cylinder arrangement; and receive a first control signal representative of the predefined amount of $CO_2$, wherein the improvement includes, among other things, a cell that produces $CO_2$ and depletes $O_2$, e.g., a direct methanol fuel cell connected to the piston/cylinder arrangement via the fluid path to flow $CO_2$ from the direct methanol fuel cell to the piston/cylinder arrangement.

Still another non-limiting embodiment of the present invention is directed to a method of operating a respiratory metabolic simulator by, among other things, providing a cell that produces $CO_2$ and depletes $O_2$, e.g., a direct methanol fuel cell having an external electrical circuit; applying an electrical load to the external electrical circuit of the cell; varying the electrical load applied to the external electrical circuit of the cell; and supplying carbon dioxide generated by the cell to respiration gases produced by the respiratory metabolic simulator, wherein by varying the electrical load, an amount of carbon dioxide generated by the cell and provided to the respiration gases produced by the respiratory metabolic simulator is controlled.

Further, another non-limiting embodiment of the present invention is directed to an improved method of delivering $CO_2$ in a respiration closed-loop control system to a respiratory simulator. The method improved by the present invention includes, among other things, providing a $CO_2$ supply to the respiratory simulator having a piston/cylinder arrangement; providing flow control hardware between the $CO_2$ supply and the piston/cylinder arrangement; generating a first control signal representative of a predefined amount of $CO_2$; moving the piston in a first direction to draw air into the piston/cylinder arrangement; providing the predefined amount of $CO_2$ into the piston/cylinder arrangement to mix the $CO_2$ and the air, whereby the release of the $CO_2$ is synchronized with a breathing pattern of the respiratory simulator; moving the piston in a second direction to empty at least a portion of the $CO_2$ and the air from the piston/cylinder arrangement; one of determining an end-tidal carbon dioxide partial pressure (Et $CO_2$) value based on an amount of $CO_2$ emptied from the piston/cylinder arrangement during an exhalation phase of the respiratory simulator; and calculating an end-tidal carbon dioxide partial pressure (Et $CO_2$) value; and generating a second control signal representative of a tidal volume and a breathing frequency representative of a physiological response to the Et $CO_2$ value to effect corresponding movement of the piston in a next inhalation and exhalation phase, wherein the improvement includes, among other things, providing a $CO_2$ supply to the respiratory simulator having a piston/cylinder arrangement by moving methanol through a direct methanol fuel cell to generate the $CO_2$, and moving the $CO_2$ through a conduit interconnecting the direct methanol fuel cell and the respiratory simulator.

DESCRIPTION OF THE PREFERRED EMBODIMENTS

Figure 1:
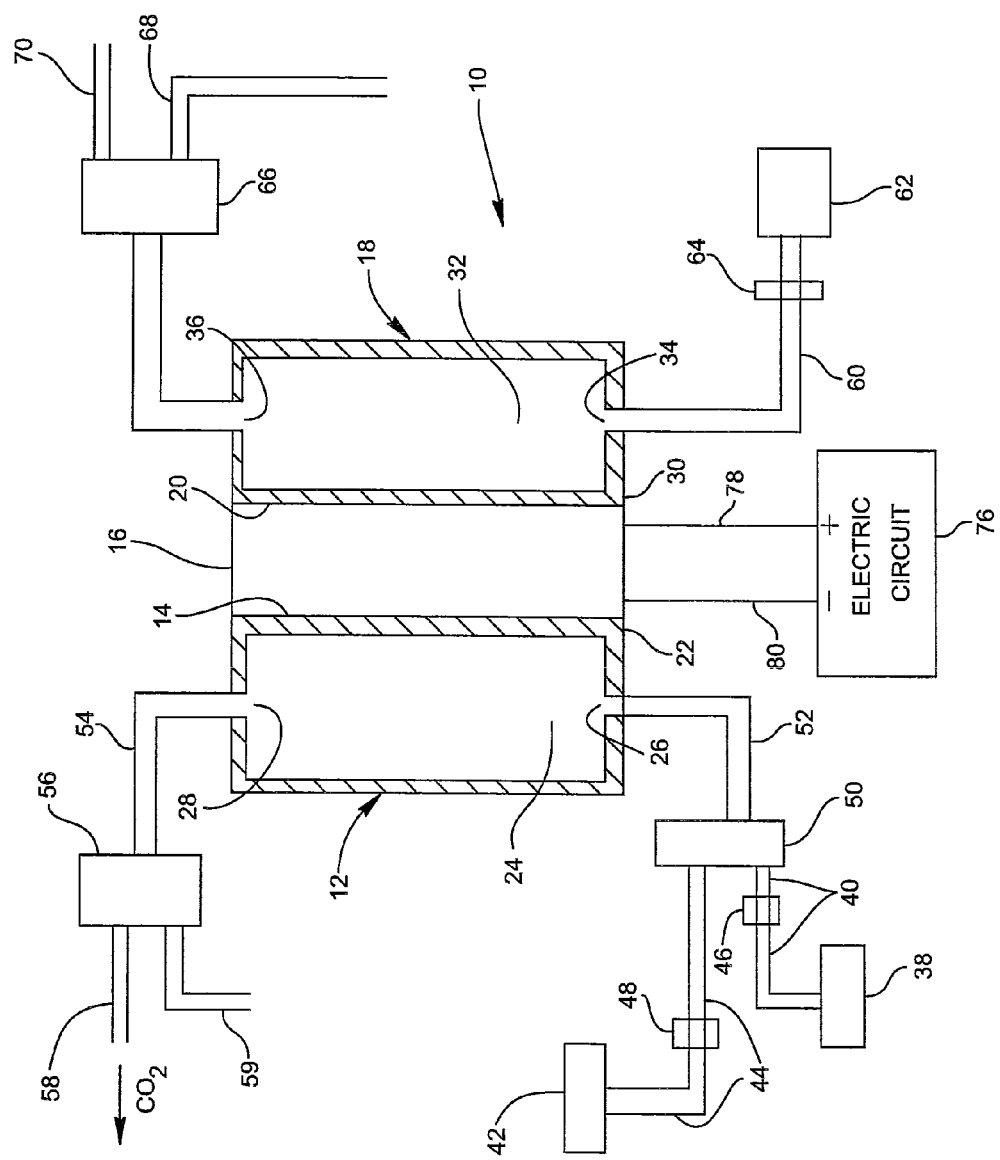
FIG. 1 is a cross-sectional view of a Direct Methanol Fuel Cell that can be used in the practice of the invention.

As used herein, spatial or directional terms, such as "inner", "outer", "left", "right", "up", "down", "horizontal", "vertical", and the like, relate to the invention as it is shown in the drawing figures. However, it is to be understood that the invention can assume various alternative orientations and, accordingly, such terms are not to be considered as limiting. Further, all numbers expressing dimensions, physical characteristics, and so forth, used in the specification and claims are to be understood as being modified in all instances by the term "about." Accordingly, unless indicated to the contrary, the numerical values set forth in the following specification and claims can vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Moreover, all ranges disclosed herein are to be understood to encompass any and all subranges subsumed therein. For example, a stated range of "1 to 10" should be considered to include any and all subranges between (and inclusive of) the minimum value of 1 and the maximum value of 10; that is, all subranges beginning with a minimum value of 1 or more and ending with a maximum value of 10 or less, e.g., 1 to 6.7, or 3.2 to 8.1, or 5.5 to 10.

Before discussing several non-limiting embodiments of the invention, it is understood that the invention is not limited in its application to the details of the particular non-limiting embodiments shown and discussed herein since the invention is capable of other embodiments. Further, the terminology used herein to discuss the invention is for the purpose of description and is not of limitation. Still further, unless indicated otherwise, in the following discussion like numbers refer to like elements.

In general, the non-limiting embodiments of the invention include, but are not limited to, the use of a cell that produces $CO_2$ and depletes $O_2$, e.g., a direct methanol fuel cell (DMFC) to provide $CO_2$ and/or to remove or deplete $O_2$ in a simulator, e.g., but not limited to, Metabolic Simulators (MS) and/or Respiratory Metabolic Simulators (RMS). Presently the use of DMFCs is mostly limited to providing an electrical power source for portable applications, e.g., to power units up to 1.5 kilowatts. The operating temperature for DMFC's is in the range of 60-130° C., but is typically around 120° C., producing an efficiency of about 40%. DMFC units are suited to portable applications and have been used in a wide variety of portable electronics products, such as mobile phones and laptop computers. The article titled "Direct Methanol Fuel Cells" by Gemma Crawley presented in *Fuel Cell Today*, dated August 2007 (wwwfuelcelltoday.com) describes a DMFC as an anode and a cathode separated by a polymer membrane electrode. A methanol and steam mixture is fed directly into the cell at the anode where the methanol is converted to $CO_2$ and hydrogen ions. The electrons created by this reaction are pushed through an external circuit, creating electricity, and returned to the cathode. The hydrogen protons pass across the polymer membrane electrolyte to the cathode where they combine with the electrons and $O_2$ to produce water. By varying the electrical load on the external circuit of the DMFC, the rate of the catalytic reaction in the DMFC can be controlled, and the amount of $CO_2$ that is produced and $O_2$ that is consumed is also controlled. For additional information regarding the DMFC, reference can be made to the article titled "Direct Methanol Fuel Cells" by Gemma Crawley, which article is hereby incorporated by reference.

In one non-limiting embodiment of the invention, a DMFC is used with a respiratory lung simulator (RLS) of the type disclosed in U.S. patent application Ser. No. 11/520,025 to Frembgen et al., now U.S. Pat. No. 7,959,443 (hereinafter also referred to as USPN '443), which documents are hereby incorporated by reference. With reference to FIG. 1, there is shown an embodiment of a DMFC 10 that can be used in the practice of the invention. The DMFC 10 includes an anode chamber 12 mounted on one side 14 of a proton exchange membrane 16, and a cathode chamber 18 mounted on an opposite side 20 of the membrane 16. The anode chamber 12 includes an anode 22 (a negative electrode) mounted on and in contact with the side 14 of the membrane 16, and a passageway 24 having an inlet opening 26 and an outlet opening 28. The cathode chamber 18 includes a cathode 30 (a positive electrode) mounted on and in contact with the side 20 of the membrane 16, and a passageway 32 having an inlet opening 34 and an outlet opening 36.

In one non-limiting embodiment of the invention, methanol ($CH_3OH$) and steam ($H_2O$) are moved into the inlet opening 26 of the passageway 24 of the anode chamber 12 from a methanol supply 38 via a conduit 40 and steam from a steam generator 42 via a conduit 44. A valve 46 is positioned on the conduit 40, and a valve 48 is positioned on the conduit 44 to regulate the flow of methanol and steam, respectively, into a mixing chamber 50. The methanol and the steam are moved from the mixing chamber 50 along a conduit 52 through the inlet opening 26 into the passageway 24 of the anode chamber 12. The outlet opening 28 of the passageway 24 of the anode chamber 12 is connected by a conduit 54 to a separator 56 to separate carbon dioxide ($CO_2$) from unused methanol and water, if any. The carbon dioxide is moved along conduit 58 to a storage arrangement or a simulator (see FIGS. 4 and 5), and the methanol and steam or water is moved along a conduit 59 for appropriate disposal or recycling.

With continued reference to FIG. 1, an oxidant, e.g., a gas or liquid containing oxygen ($O_2$), is moved into the inlet opening 34 of the passageway 32 of the cathode chamber 18 from a conduit 60 connected to a supply 62 of the oxidant. A valve 64 is provided on the conduit 60 to control the flow of oxidant into the passageway 32 of the cathode chamber 18. Water and unused oxidant are moved through the exit opening 36 of the passageway 32 of the cathode chamber 18 to a separator 66 to separate the water and the unused portion of the oxidant, e.g., the gas or liquid, less the oxygen removed as the oxidant moved through the passageway 32. The water from the separator 66 is moved along a conduit 68 and is discarded or moved to the steam generator 42, and the unused portion of the oxidant moved along a conduit 70 to a predetermined usage.

An electric load circuit 76 is connected by wires 78 and 80 to the membrane 16 to move electrons from the anode 22 to the cathode 30 as the methanol and water move through the passageway 24 of the anode chamber 12, and the oxidant moves through the passageway 32 of the cathode chamber 18.

In the use of the DMFC 10, a mixture of methanol and water is moved through the passageway 24 of the anode chamber 12, and an oxidant is moved through the passageway 32 of the cathode chamber 18. As the methanol and water move through passageway 24, the chemical reaction shown by Equation (1) takes place, and as the oxidant moves through the passageway 32, the chemical reaction shown by Equation (2) takes place.

$$CH_3OH + H_2O = 6H^+ + 6e^- + CO_2 \qquad \text{Equation (1)}$$

$$3/2 O_2 + 6H^+ + 6e^- = 3H_2O \qquad \text{Equation (2)}$$

The overall reaction is shown by Equation (3).

$$CH_3OH + 3/2 O_2 = 2H_2O + CO_2 \qquad \text{Equation (3)}$$

The operation of DMFCs are well known in the art, and no further discussion regarding the operation and components of DMFC are deemed necessary.

The discussion is now directed to a non-limiting embodiment of the invention to use the DMFC 10 shown in FIG. 1 with the human respiratory process disclosed in USPN '443. More particularly, USPN '443 provides a detailed description of the human respiratory process, the general operation of a Respiratory Lung Simulator (RLS), and the methods for determining and controlling the respiratory gas compositions. Of interest in the present discussion are the methods for determining and controlling the respiratory gas compositions disclosed in USPN '443. More particularly, USPN '443 discloses the supply of $CO_2$ to the respiratory gases from an external source, e.g., the $CO_2$ is provided in a gas cylinder and no facilities are provided for the removal of $O_2$. In the case of the RLS of the present invention, $CO_2$ is supplied and $O_2$ is removed by the catalytic low-temperature (60-130° C.) reaction of the DMFC 10 or another hydrocarbon-fueled cell.

Figure 2:
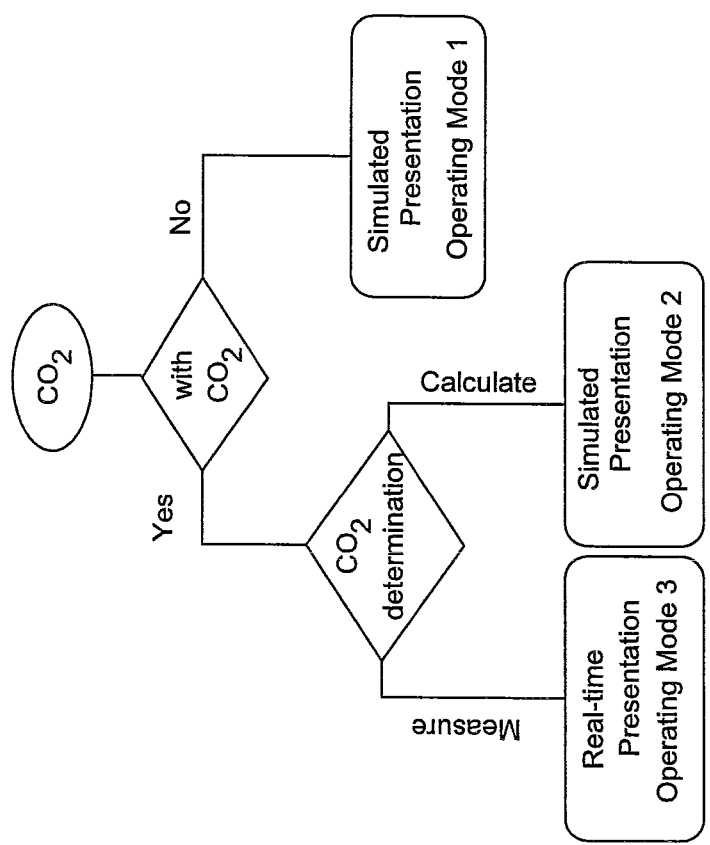
FIG. 2 is a prior art flow chart for selecting operating modes that can be used in the practice of the invention.

The RLS disclosed in USPN '443 provides for three operating modes that are available for the simulation of a $CO_2$ response. These three operating modes correspond to different simulation requirements, namely, the measurement of the $CO_2$ partial pressure, the calculation of the $CO_2$ partial pressure, and the simulation of the $CO_2$ flow. These operating modes allow the lung simulation to be used in the areas of development, training, and teaching, for example and not limiting to the invention, so that the use of carbon dioxide is not necessary when the system is used as a teaching tool. FIG. 2 (FIG. 10 of USPN '443) depicts the ability to select between the various operating modes of the RMS. For example, in Operating Mode 1, the RMS does not use $CO_2$, but rather the $CO_2$ flow is simulated, and the software of the RMS then calculates a $CO_2$ partial pressure. In Operating Mode 2, the RMS is conducted with $CO_2$. The same algorithm used in Operating Mode 1 can be used for the calculation of the $CO_2$ partial pressure. The Operating Mode 2 also addresses the $CO_2$ flow control. In this operating mode, external units that determine the $CO_2$ partial pressure can be used. For example, it is possible to record capnograms of the respiratory air expired from the RMS. In Operating Mode 3, the $CO_2$ partial pressure (Et $CO_2$) is measured, e.g., with an infrared sensor (not shown). The measured Et $CO_2$ value is transmitted to a control algorithm, which is integrated in the software. The control algorithm controls the tidal volume as well as the respiration frequency, and a capnogram recorded by the sensor is simultaneously displayed.

Figure 3:
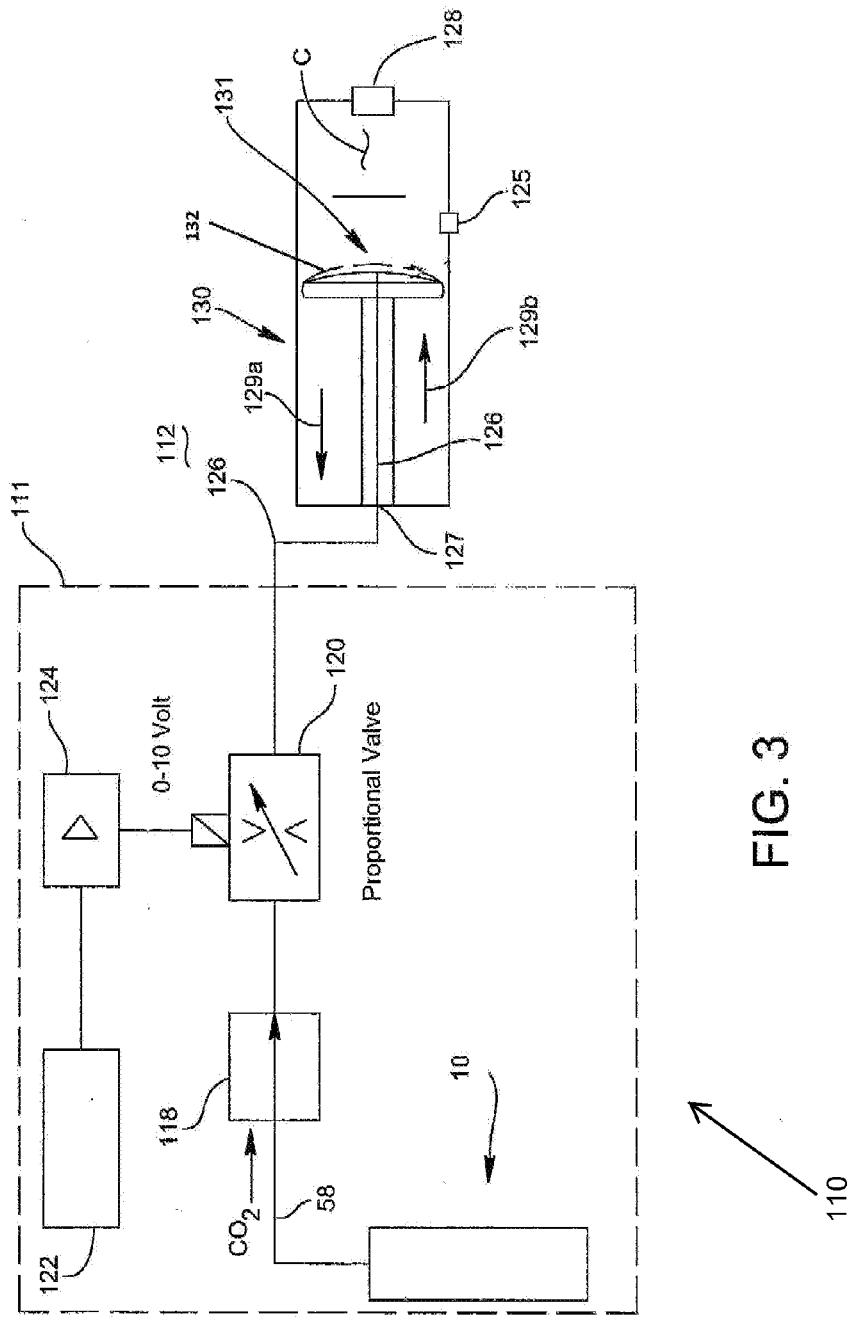
FIG. 3 is a schematic of non-limiting embodiment of a $CO_2$ flow control hardware incorporating features of the invention.

As shown in FIG. 3, the RLS of USPN '443 utilizes flow control hardware 110 which controls and introduces the desired quantity of $CO_2$. The area inside the broken line represents $CO_2$ flow control 111, and the area outside the broken line represents the $CO_2$ application 112. The $CO_2$ is moved from the DMFC 10 through a conduit 58 to a pressure regulator 118.

The pressure regulator 118 moves the $CO_2$ under a predetermined pressure, for example but not limited to, 4 bar to a proportional valve 120, e.g., one manufactured by Asco-Joucomatic, however, it is to be understood that any suitable proportional valve may be used. In a non-limited embodiment of the invention, the proportional valve 120 is actuated with a multi-function data reception card 122, such as that supplied by National Instruments, that is integrated into the computer and controlled by software thereof. The data reception card 122 includes two analog outputs and is configured to output a predetermined voltage, for example, but not limited to the discussion, between 0 and 2 volts. The voltage can be adjusted by the user proportionally to the desired $CO_2$ flow. The resultant signal is adjusted via an amplifier circuit 124 designed for valve actuation.

With continued reference to FIG. 3, the $CO_2$ application 112 is not limiting to the invention and can be any type of lung simulator known in the art, for example but not limited to, Active Servo Lung 5000 (ASL 5000), marketed by IngMar Medical, Ltd. of Pittsburgh, Pa. The general principle of operation of the ASL 5000 is described in detail in U.S. Pat. No. 5,975,748 to East, I V et al., the contents of which are incorporated herein by reference. The ASL 5000 includes a piston/cylinder arrangement 130 for receiving air therein. The invention, however, is not limited to the ASL 5000 and can be used with any type of lung simulator using any type of arrangement for containing air, e.g., bellows. The piston/cylinder arrangement 130 includes a piston 131. A diffusing surface 132 can be situated within the piston/cylinder arrangement 130 for distributing the $CO_2$ within the cylinder. The piston/cylinder arrangement 130 receives the air via an inlet 125 and provides the air into a cylinder chamber C. Preferably, a controlled application of $CO_2$ into the chamber C is carried out to achieve the maximum possible mixing with the air. Accordingly, $CO_2$ is introduced into the chamber C from the flow control 111 via a fluid path 126 (such as flexible tubing) connected to an inlet 127 of the piston/cylinder arrangement 130. An outlet 128 of the piston/cylinder arrangement 130 is used to release the air and the $CO_2$. In operation, movement of the piston 131 in a direction 129a corresponds to inhalation and results in the introduction of the air into the chamber C. Conversely, movement of the piston 131 in a direction 129b corresponds to exhalation and results in the release or exhaust of the air and the $CO_2$ from the chamber C.

Desirably, the requirement for a $CO_2$ application is the smallest possible deviation of the $CO_2$ flow from the specified flow. In addition, the maximum deviation preferable should not have any significant effect on the respiratory response. In a desirable embodiment, the maximum $CO_2$ flow into the piston/cylinder arrangement 130 is one liter per minute and the minimum flow is 100 milliliters ("ml") per minute. The lower limit of 100 ml per minute may be the smallest flow that can be set, and the upper limit of one liter per minute may result from the limitation of the existing lung simulator, e.g., the ASL 5000, to simulate a sufficiently large tidal volume as well as a significantly high respiration frequency.

Figure 4:
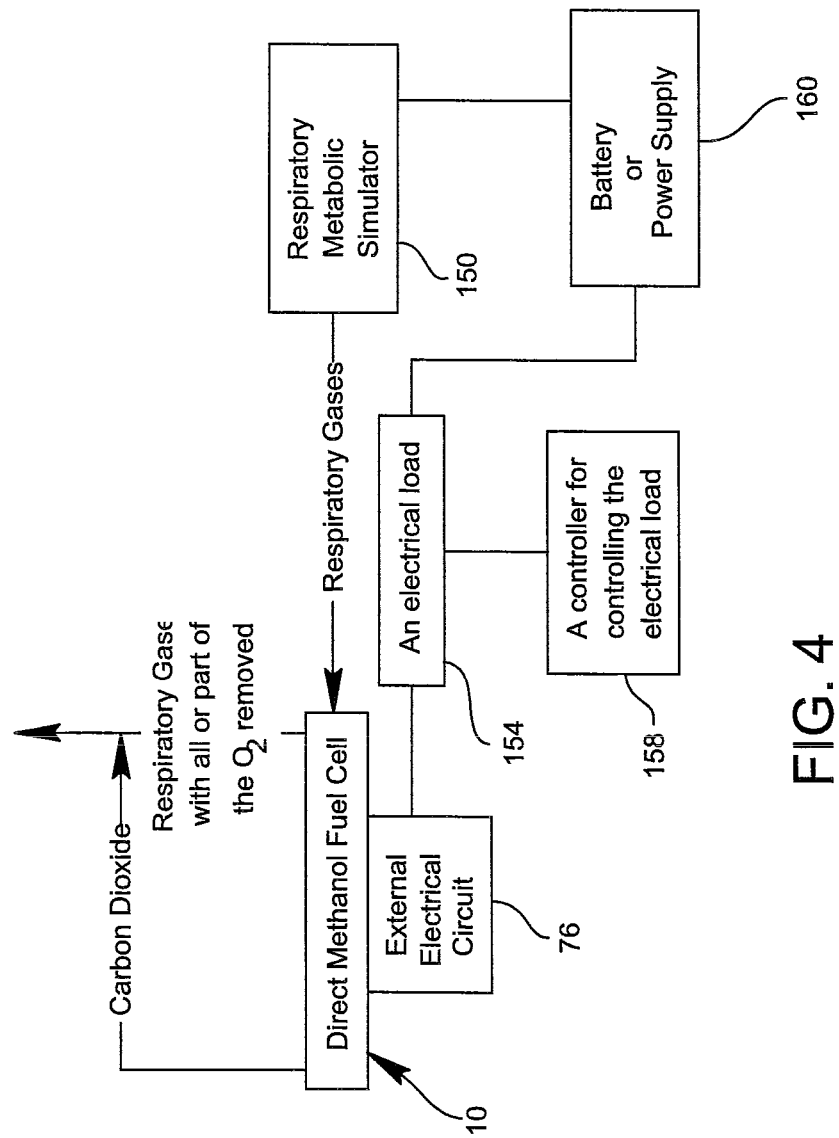
FIG. 4 is a schematic representation of a non-limiting embodiment of a respiratory metabolic simulator incorporating features of the invention.

Shown in FIG. 4 is an RMS 150, which avoids the shortcomings of the prior art by employing the catalytic low-temperature (60-130° C.) reaction of the DMFC 10 (see FIG. 1) or another hydrocarbon-fueled cell to supply $CO_2$ and/or remove $O_2$ from the respiratory gases in accordance to the teachings of the invention. In order to quantitatively control the simulated metabolic rate through appropriate additions of $CO_2$ and/or removal of $O_2$ to the respiratory gases, a suitable electrical load 154 is attached to the external electrical circuit or electric load circuit 76 of the DMFC 10 to consume the electricity created by the catalytic reaction taking place in the DMFC 10. Suitable electronics, i.e., a controller 158, are also provided to remotely vary the electrical load that is required by the electrical load circuit 154. The necessary $CO_2$ addition and/or $O_2$ removal required for the desired metabolic simulation is determined using the methods described in Frembgen or another suitable method. The controller 158 is then used to set the electrical load of the electrical load circuit 154 at a level that will generate the desired amount of $CO_2$ and/or utilize the desired amount of $O_2$. By controlling the electrical load on the external electrical circuit 76 of the DMFC 10 and, thus, the catalytic reaction rate in the DMFC 10, the generation of $CO_2$ and $O_2$ by the DMFC 10 can be controlled to achieve the desired simulated metabolic rate.

Figure 5:
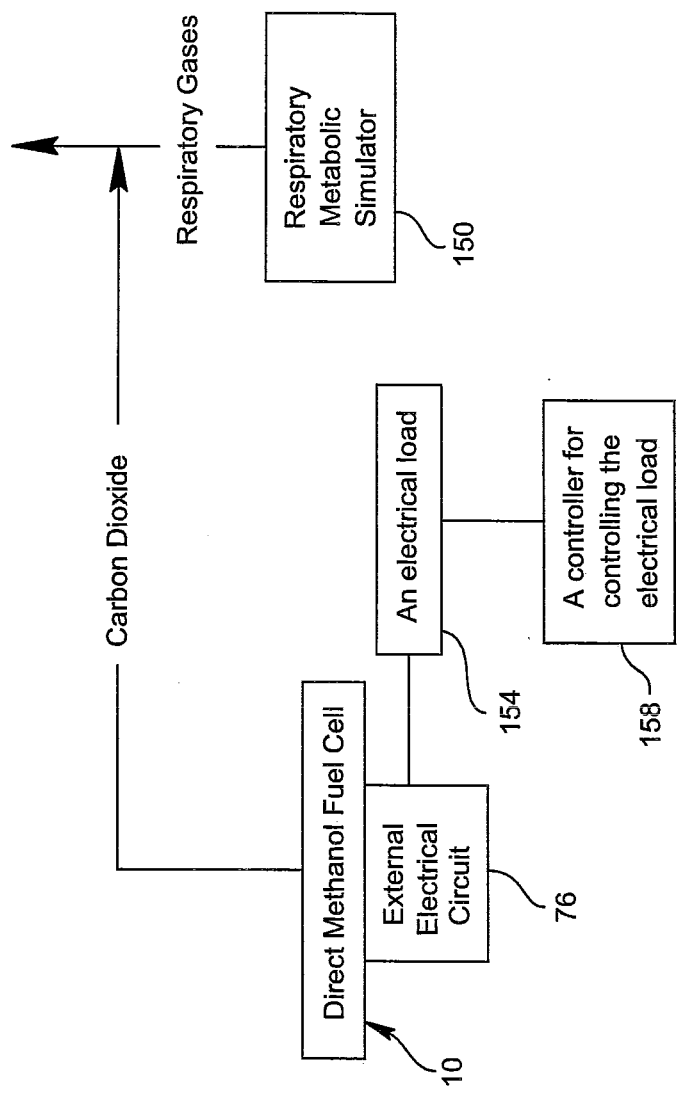
FIG. 5 is a schematic representation of another non-limiting embodiment of a respiratory metabolic simulator incorporating features of the invention.

While FIGS. 1, 3, and 4 show non-limiting embodiments of the invention where the DMFC 10 is utilized to provide $CO_2$ to the respiratory gases, FIG. 5 shows a non-limiting embodiment of the invention where the DMFC 10 is also used to remove $O_2$ from the respiratory gases from the RMS. More particularly, as shown in FIGS. 1 and 5, the respiratory gases (an oxidant) from the RMS are moved through the conduit 60 into the passageway 32 over the cathode 30 of the cathode chamber 18 of the DMFC 10 to remove the $O_2$ from respiratory gases from the RMS. The $CO_2$ from the conduit 58 (FIG. 1) produced by the DMFC 10 is mixed with the oxygen-reduced respiratory gases from the RMS 150 (see FIG. 5).

While the external electrical circuit 76 can be designed in any manner that utilizes electricity and allows for the electrical load circuit 154 to be varied, it can be advantageously used to supply energy for operation of the RMS 150. For example, the electrical load circuit 76 can be designed to charge a battery or support a power supply 160 used in the operation of the RMS 150. Alternatively, the electrical load circuit 154 can be designed to include a heater with convective, evaporative, and/or radiant heat components to supply the required thermal metabolism of the RMS 150 and/or humidify the exhalation gas. Water for humidification is available intrinsically, as it is a byproduct of catalytic reaction in the fuel cell.

As can now be appreciated, the invention can be combined with both an anatomically-correct human patient simulator as well as with functionally correct respiratory/breathing simulators to increase the fidelity of such simulators in rendering a patient which has the expected outputs for respiratory gases and temperature.

Further, the invention is not limited to the non-limiting embodiments of the invention discussed above, and the scope of the invention is only limited by the scope of the following claims.

The invention claimed is:

1. An improved system for delivering $CO_2$ in a respiration closed-loop control system to a respiratory simulator, the system comprising:
    a piston/cylinder arrangement having a first inlet for receiving a volume of air during an inhalation phase, a second inlet for receiving $CO_2$, and an outlet for releasing the air containing $O_2$ and $CO_2$ therethrough during an exhalation phase;
    a supply of $CO_2$, the supply of $CO_2$ connected to the piston/cylinder arrangement via a fluid path;
    a valve situated along the fluid path between the supply of $CO_2$ and the piston/cylinder arrangement;
    a diffusing surface situated within the piston/cylinder arrangement for distributing the $CO_2$ within the cylinder of the piston/cylinder arrangement; and
    a controller configured to actuate the valve to allow a predefined amount of $CO_2$ to flow into the piston/cylinder arrangement and receive a first control signal representative of the predefined amount of $CO_2$,
    wherein the improvement comprises:
    the supply of $CO_2$ is provided by a direct methanol fuel cell that produces $CO_2$ and provides water and an unused oxidant from the air during the inhalation phase, wherein the direct methanol fuel cell is connected to the piston/cylinder arrangement via the fluid path to flow $CO_2$ from the direct methanol fuel cell to the piston/cylinder arrangement, and to flow the water and unused oxidant to a separator to separate the unused oxidant and the water, wherein a portion of $O_2$ of the volume of air provided to the piston/cylinder arrangement during inhalation phase is first used by the direct methanol fuel cell to produce $CO_2$ and $H_2O$, and wherein the improvement further comprises a load circuit coupled to the direct methanol fuel cell to supply energy to the system, the load circuit controlled by the controller, wherein by controlling the load circuit $CO_2$ and $O_2$ of the respiration closed-loop control system can be varied.

2. The improved system according to claim 1, wherein the controller is configured to actuate the valve after the inhalation phase to allow a predefined amount of $CO_2$ to flow into the piston/cylinder arrangement to mix with the volume of air forming a volume containing the air and the added $CO_2$ to be released from the piston/cylinder arrangement in the exhalation phase thereof, wherein the predefined amount of $CO_2$ in combination with the air received during the inhalation phase emulates an amount of $CO_2$ released in an exhalation phase of a patient, and wherein only $CO_2$ is added to the air in the piston/cylinder arrangement prior to the exhalation phase of the piston/cylinder arrangement.

3. The improved system according to claim 1, wherein the direct methanol fuel cell is the sole source of $CO_2$ supplied to the respiratory simulator.

4. A An improved method of delivering $CO_2$ in a respiration closed-loop control system to a respiratory simulator, the method comprising:
    providing a $CO_2$ supply to the respiratory simulator having a piston/cylinder arrangement;
    providing flow control hardware between the $CO_2$ supply and the piston/cylinder arrangement;
    generating a first control signal representative of a predefined amount of $CO_2$;

moving the piston of the piston/cylinder arrangement in a first direction to draw a volume of air into the piston/cylinder arrangement during an inhalation phase;

providing the predefined amount of $CO_2$ into the piston/cylinder arrangement after the inhalation phase to mix the $CO_2$ and the air forming a volume containing air containing $O_2$ and the added $CO_2$ to be released in an exhalation phase, wherein only the $CO_2$ is added to the air in the piston/cylinder arrangement prior to the exhalation phase, whereby the release of the $CO_2$ is synchronized with a breathing pattern of the respiratory simulator;

moving the piston of the piston/cylinder arrangement in a second direction to empty the volume of air including $O_2$ and the added $CO_2$ from the piston/cylinder arrangement in the exhalation phase, wherein the predefined amount of $CO_2$ in combination with the air received during the inhalation phase emulates an amount of $CO_2$ released in an exhalation phase of a patient; and determining an end-tidal carbon dioxide partial pressure (Et $CO_2$) value based on an amount of $CO_2$ emptied from the piston/cylinder arrangement during an exhalation phase of the respiratory simulator, and calculating an end-tidal carbon dioxide partial pressure (Et $CO_2$) value;

wherein the improvement comprises:

providing a $CO_2$ supply to the respiratory simulator having a piston/cylinder arrangement by moving methanol through a direct methanol fuel cell to generate $CO_2$ and water containing unused oxidant from the air during the inhalation phase, and moving $CO_2$ through a conduit interconnecting the direct methanol fuel cell and the respiratory simulator, and moving the water containing unused oxidant to a separator to separate the water and the unused oxidant, wherein a portion of $O_2$ of the air during inhalation phase is first used by the direct methanol fuel cell to produce $CO_2$ and $H_2O$, and wherein the improvement further comprises a load circuit coupled to the direct methanol fuel cell to supply energy to the system, the load circuit controlled by a controller, wherein by controlling the load circuit $CO_2$ and $O_2$ of the respiration closed-loop control system can be varied.

5. The improved method of claim 4, wherein the predefined amount of $CO_2$ is a function of moved volume and concentration of the $CO_2$ emptied from the piston/cylinder arrangement.

6. The improved method of claim 4, wherein the direct methanol fuel cell is the sole source of $CO_2$ supplied to the respiratory simulator.

* * * * *

UNITED STATES PATENT AND TRADEMARK OFFICE
CERTIFICATE OF CORRECTION

PATENT NO. : 9,463,292 B2
APPLICATION NO. : 13/232662
DATED : October 11, 2016
INVENTOR(S) : Stefan Frembgen Page 1 of 1

It is certified that error appears in the above-identified patent and that said Letters Patent is hereby corrected as shown below:

In the Claims

Column 8, Line 59, Claim 4, before "An" delete "A"

Signed and Sealed this
Twentieth Day of December, 2016

Michelle K. Lee
*Director of the United States Patent and Trademark Office*